US005747319A

United States Patent [19]
Au-Young et al.

[11] Patent Number: 5,747,319
[45] Date of Patent: May 5, 1998

[54] HUMAN MRNA EDITING ENZYME

[75] Inventors: Janice Au-Young, Berkeley; Phillip R. Hawkins, Mountain View; Jennifer L. Hillman, San Jose, all of Calif.

[73] Assignee: Incyte Pharmaceuticals, Inc., Palo Alto, Calif.

[21] Appl. No.: 687,895

[22] Filed: Jul. 25, 1996

[51] Int. Cl.$^6$ ............................ C12N 9/22; C12N 15/63; C12N 5/00; C07H 21/04

[52] U.S. Cl. .................. 435/199; 435/240.1; 435/243; 435/252.3; 435/254.11; 435/320.1; 435/325; 435/410; 536/23.2

[58] Field of Search .................. 435/199, 320.1, 435/240.1, 325, 410, 243, 252.3, 254.11; 536/23.2

[56] References Cited

U.S. PATENT DOCUMENTS

| | | | |
|---|---|---|---|
| 5,389,514 | 2/1995 | Taylor | 435/6 |
| 5,434,058 | 7/1995 | Davidson | 435/69.1 |
| 5,550,034 | 8/1996 | Teng et al. | 435/69.1 |
| 5,643,778 | 7/1997 | Nishikura | 435/227 |

OTHER PUBLICATIONS

Navaratnam, N., et al., "Evolutionary Origins of apoB mRNA Editing: Catalysis by a Cytidine Deaminase That Has Acquired a Novel RNA-Binding Motif at Its Active Site" *Cell*, 81:187–195 (1995).

Davidson, N.O., "Apolipoprotein B mRNA Editing: A Key Controlling Element Targeting Fats to Proper Tissue" *Ann. Med.*, 25:539–543 (1993).

Hadjiagapiou, C., et al., "Molecular cloning of a human small intestinal apolipoprotein B mRNA editing protein" *Nucleic Acids Res.*, 22:1874–1879 (1994).

Teng, B., et al., "Molecular Cloning of an Apolipoprotein B Messenger RNA Editing Protein" *Science*, 260:1816–1819 (1993).

MacGinnitie, A., et al., "Mutagenesis of apobec-1, the Catalytic Subunit of the Mammalian Apolipoprotein B mRNA Editing Enzyme, Reveals Distinct Domains That Mediate Cytosine Nucleoside Deaminase, RNA Binding, and RNA Editing Activity" *J. Biol. Chem.*, 270:14768–14775 (1995).

Yamanaka, S., et al., "Cloning and Mutagenesis of the Rabbit ApoB mRNA Editing Protein" *J. Biol. Chem.*, 269:21725–21734 (1994).

Hodges, P., et al., "Apolipoprotein B mRNA editing: a new tier for the control of gene expression" *Trends Biochem. Sci.*, 17:77–81 (1992).

Woolf, T.M., "Toward the therapeutic editing of mutated RNA sequences" *Proc. Natl. Acad. Sci.*, 92:8298–8302 (1995).

Young, S.G., "Recent Process in Understanding Apolipoprotein B" *Circulation*, 82:1574–1594 (1990).

Innerarity, T.L., et al., "Mutations and Variants of Apolipoprotein B that Affect Plasma Cholesterol Levels" *Adv. Exp. Med. Biol.*, 285:25–31 (1991).

Teng, B., et al., "Adenovirus-mediated Gene Transfer of Rat Apolipoprotein B mRNA-editing Protein in Mice Virtually Eliminates Apolipoprotein B–100 and Normal Low Density Lipoprotein Production" *J. Biol. Chem.*, 269:29395–29404 (1994).

Novo, F.J., et al., "Editing of human α-galactosidase RNA resulting in a pyrimidine to purine conversion" *Nucleic Acids Res.*, 23:2636–2640 (1995).

Kim, U., et al., "Purification and Characterization of Double-stranded RNA Adenosine Deaminase from Bovine Nuclear Extracts" *J. Biol. Chem.*, 269:13480–13489 (1994).

Nutt, S.L., et al., "Differential RNA editing efficiency of AMPA receptor subunit GluR-2 in human brain" *NeuroReport*, 5:1679–1683 (1994).

Melcher, T., et al., "A mammalian RNA editing enzyme" *Nature*, 379:460–464 (1996).

Madsen, P.P., (GI 436941), GenBank Sequence Database (Accession 436941), National Center for Biotechnology Information, National Library of Medicine, Bethesda, Maryland 20894 (1993).

Hadjiagapiou et al. (May 25, 1994) Molecular cloning of a human small intestinal apolipoprotein B mRNA editing protein, Nucleic Acids Research 22(10):1874–1879.

*Primary Examiner*—Robert A. Wax
*Assistant Examiner*—Einar Stole
*Attorney, Agent, or Firm*—Lucy J. Billings

[57] ABSTRACT

The present invention provides a polynucleotide which identifies and encodes a novel human mRNA editing enzyme (REE). The invention provides for genetically engineered expression vectors and host cells comprising the nucleic acid sequence encoding REE. The invention also provides for the use of substantially purified REE and its agonists, antagonists, or inhibitors in the commercial production of recombinant proteins and in pharmaceutical compositions for the treatment of diseases associated with the expression of REE. Additionally, the invention provides for the use of antisense molecules to REE in pharmaceutical compositions for treatment of diseases associated with the expression of REE. The invention also describes diagnostic assays which utilize diagnostic compositions comprising the polynucleotide, fragments or the complement thereof, which hybridize with the genomic sequence or the transcript of polynucleotides encoding REE or anti-REE antibodies which specifically bind to REE.

7 Claims, 8 Drawing Sheets

```
                  9              18          27          36          45          54
5' NTG NCG CNC TAT ATG CTT GGC NTC CTC CGN GAA CCT GTC ATC CCG GCN CCA TTT 63              72          81          90          99         108
   NAN NAG CTG ACA GCT GCT TGG GAC TCT GCC GCC AGG GCC TGG CCC AGA CCT GCC 117             126         135         144         153         162
   TGC CTC TCT CCT CTC CAG TGA CTG AGC CTG CAC AGC CCC TCC ATG GCC CAG
                                                                 M   A   Q 171             180         189         198         207         216
   AAG GAA GCT GCT GTG GCC ACT GAG GCT GCC TCC CAG AAT GGG GAG GAT CTG
    K   E   A   A   V   A   T   E   A   A   S   Q   N   G   E   D   L 225             234         243         252         261         270
   GAG AAC CTG GAC GAC CCT GAG AAG CTG AAA GAG ATT GAG CTG CCG CCC TTT
    E   N   L   D   D   P   E   K   L   K   E   I   E   L   P   P   F 279             288         297         306         315         324
   GAG ATT GTC ACA GGA GAA CGG CTG CCT GCC AAC TTC TTT AAA TTC CAG TTC CGG
    E   I   V   T   G   E   R   L   P   A   N   F   F   K   F   Q   F   R 333             342         351         360         369         378
   AAT GTG GAG TAC AGT TCC GGG AGG AAC AAG ACC TTC CTC TGC TAT GTG GTT GAA
    N   V   E   Y   S   S   G   R   N   K   T   F   L   C   Y   V   V   E
```

FIGURE 1A

| | | | 387 | | | | 396 | | | 405 | | | 414 | | | 423 | | | 432 |
|---|---|---|---|---|---|---|---|---|---|---|---|---|---|---|---|---|---|---|---|
| GCA | CAG | AAG | GGC | AAG | GGG | GGC | CAA | GTG | CAG | GCA | TCT | CGG | GGA | TAC | CTA | GAG | GAT | GAG |
| A | Q | K | G | K | G | G | Q | V | Q | A | S | R | G | Y | L | E | D | E |
| | | | 441 | | | | 450 | | | 459 | | | 468 | | | 477 | | | 486 |
| CAT | GCG | GCT | GCC | CAT | GCA | GAG | GAA | GCT | TTC | TTC | AAC | ACC | ATC | CTG | CCA | GCC | TTC |
| H | A | A | A | H | A | E | E | A | F | F | N | T | I | L | P | A | F |
| | | | 495 | | | | 504 | | | 513 | | | 522 | | | 531 | | | 540 |
| GAC | CCA | GCC | CTG | CGG | TAC | AAT | GTC | ACC | TGG | TAT | GTG | TCC | TCC | AGC | CCC | TGT | GCA |
| D | P | A | L | R | Y | N | V | T | W | Y | V | S | S | S | P | C | A |
| | | | 549 | | | | 558 | | | 567 | | | 576 | | | 585 | | | 594 |
| GCG | TGT | GCT | GAC | CGC | ATT | AYC | AAA | ACC | CTT | AGC | AAG | ACC | AAG | AAC | CTG | CGT | CTG |
| A | C | A | D | R | I | X | K | T | L | S | K | T | K | N | L | R | L |
| | | | 603 | | | | 612 | | | 621 | | | 630 | | | 639 | | | 648 |
| CTC | ATT | CTG | GTG | GGT | CGA | CTC | TTC | ATG | TGG | GAG | GAG | CCG | GAG | ATC | CAG | GCT | GCT |
| L | I | L | V | G | R | L | F | M | W | E | E | P | E | I | Q | A | A |
| | | | 657 | | | | 666 | | | 675 | | | 684 | | | 693 | | | 702 |
| CTG | AAG | AAG | CTG | AAG | GAG | GCT | GGC | TGT | AAA | CTG | CGC | ATC | ATG | AAG | CCC | CAG | GAC |
| L | K | K | L | K | E | A | G | C | K | L | R | I | M | K | P | Q | D |
| | | | 711 | | | | 720 | | | 729 | | | 738 | | | 747 | | | 756 |
| TTC | GAA | TAT | GTC | TGG | CAG | AAT | TTT | GTG | GAG | CAA | GAA | GAG | GGT | GAA | TCC | AAG | GCC |
| F | E | Y | V | W | Q | N | F | V | E | Q | E | E | G | E | S | K | A |

FIGURE 1B

```
           765             774             783             792             801             810
TTT CAR CCC TGG GAG GAC ATT CAG GAG AAC TTC CTA TAC GAG GAG AAG TTG
 F   Q   P   W   E   D   I   Q   E   N   F   L   Y   E   E   K   L 819             828             837             846             855             864
GCA GAC ATC TGA AGT AGG GCA ACT GGG TTT CCT CAC GGA TTC CTG TCT GCC ACC
 A   D   I 873             882             891
AAG AGA CAG CAA TGC ATG TAC AGC CAT T 3'
```

FIGURE 1C

The Electronic Northern for Clone: 057953
and Stringency >= 50

| Library | Lib Description | Abun | Pct Abun |
|---|---|---|---|
| MUSCNOT01 | muscle, skeletal | 1 | 0.0444 |
| PROSNOT07 | prostate, 69 M, match to PROSTUT05 | 1 | 0.0347 |

```
194 Q E E G E S K A F Q P - W E D I - - - - - - - - - - - - - - - - - - - - - Q E  SEQ ID NO:1
 85 R Q G C - - - - P F Q P - W D G L - - - - - - - - - - - - - - - - - - - - - E E  SEQ ID NO:3
162 G D E A H W P Q Y P P L W M M L Y A L E L H C I I L S L P P C L K I S R R W Q N  SEQ ID NO:4
162 S N E A H W P R Y P H L W V R L Y V L E L Y C I I L G L P P C L N I L R R K Q P  SEQ ID NO:5

211 N F L Y Y E E K L A D - - - - - I - - - - - - - - - - - - - - - - - - - - - -  SEQ ID NO:1
 99 H S Q A L S G R L R A - - - - - I L Q N Q G - - - - - - - - - - - - - - - N -  SEQ ID NO:3
202 H L T F F R L H L Q N C H Y Q T I P P H I L L A T G L I H P S V A W R - - - - -  SEQ ID NO:4
202 Q L T F F T I A L Q S C H Y Q R L P P H I L W A T G L - - - - - - - - - - - K -  SEQ ID NO:5
```

FIGURE 3B

HUMAN MRNA EDITING ENZYME

FIELD OF THE INVENTION

The present invention relates to nucleic acid and amino acid sequences of a novel human mRNA editing enzyme and to the use of these sequences in the diagnosis, study, prevention and treatment of disease.

BACKGROUND OF THE INVENTION

Apolipoprotein B (apo B) circulates in two distinct forms referred to as apo B100 and apo B48. Apo B48 is encoded by same gene as apo B100 and arises as a result of mRNA editing. A single cytidine nucleotide in apo B100 mRNA is deaminated by a zinc-containing enzyme, resulting in a CAA to UAA-stop codon change (Navaratnam N et al (1995) Cell 81: 187–195). RNA editing of apo B has important consequences in the catabolism of plasma lipoproteins and the ability to generate hybrid lipoproteins (Davidson NO (1993) Ann Med 25: 539–53).

Hadjiagapiou C et al (1994, Nucleic Acids Res 22: 1874–1879) cloned the apo B mRNA editing protein (HEPR) from human small intestine cDNA. HEPR is the catalytic subunit of an enzyme complex which includes, yet to be identified, complementation factors (Teng B et al (1993) Science 260: 1819). HEPR contains consensus phosphorylation sites as well as conserved histidine and cysteine residues identified as a $Zn^{2+}$ binding motif in other cytidine deaminases. Mutational studies indicated that the putative zinc-cytidine coordinating residues His61, Cys93, and Cys96 and the catalytically active residues Glu63 and Pro92 are necessary for both RNA editing and cytidine deaminase activities (MacGinnitie et al (1995) J Biol Chem 270: 14768–14775). His6t is also required for RNA binding activity.

HEPR is expressed in the adult small intestine and to a much lesser extent in the stomach, colon, and testis (Hadjiagapiou et al, supra). The rabbit homolog of HEPR is only expressed in the small and large intestine, while the complementation proteins, essential for RNA editing, were found to exist in a wide range of organs that do not express apo B, suggesting additional RNA editing enzymes with a more widespread role in the generation of RNA and protein diversity (Yamanaka S et al (1994) J Biol Chem 269: 21725–21734; Hodges P et al (1992) Trends Biochem Sci 17: 77–81).

mRNA Editing Enzymes and Disease

The principle of therapeutic RNA editing was demonstrated by using cell extracts containing an RNA editing enzyme to correct an aberrant stop codon introduced into synthetic RNA encoding dystrophin protein (Woolf TM et al (1995) PNAS USA 92: 8298–8302). Deamination of a nucleotide in a stop codon resulted in translation read-through and a dramatic increase in expression of a downstream gene.

Apo B editing is a mechanism which determines how much apo B48 is synthesized in place of apo B100 in a specific tissue. Apo B100 is the exclusive apolipoprotein of low density lipoproteins, which transport most of the plasma cholesterol in humans. In contrast, apo B48 is directed to chylomicrons, triglyceride-rich lipoproteins that transport dietary lipids and undergo catabolic clearance much faster than particles containing apo B100 (Young S G (1990) Circulation 82: 1574–1594). Apo B editing has major physiological and clinical implications. All apo B100 containing lipoproteins are atherogenic, especially when present in high concentrations. Alterations in apo B100 can cause either hypocholesterolemia or hypercholesterolemia (Innerarity T L et al (1991) Adv Exp Med Biol 285: 25–31). Apo B mRNA editing down-regulates the amount of apo B100 production. Somatic gene transfer of rat REPR, the rat homolog of HEPR, into the liver of mice essentially eliminates apo B100 and plasma low-density lipoprotein without affecting anti-atherogenic high density lipoproteins (Teng B et al (1994) J Biol Chem 269: 29395–29404).

Alpha-galactosidase is a lysosomal enzyme that is deficient in patients with Fabry's disease. After excluding other possibilities, Novo F J et al (1995, Nucleic Acids Res 23: 2636–2640) proposed that RNA editing is responsible for an observed nucleotide conversion in alpha-galactosidase mRNA from Fabry's disease patients. The enzyme responsible for the nucleotide conversion has not been identified.

Among the main characteristics of psoriasis are abnormal keratinocyte proliferation and differentiation. A search for proteins that are implicated in psoriasis yielded a partial sequence for phorbolin I, a protein upregulated in psoriatic keratinocytes (Madsen P P, unpublished).

Deamination of RNA nucleotides occurs in the brain. RED1, a double stranded RNA adenosine deaminase expressed in brain and peripheral tissue, edits the channel determinant site in glutamate receptor pre-mRNA. This site controls the $Ca^{2+}$ permeability of alpha-amino-3-hydroxy-5-methylisoxazole-4-propionic acid (AMPA) receptors. Another double stranded RNA adenosine deaminase, DRADA, edits a different site in the glutamate receptor pre-mRNA (Kim U et al (1994) J Biol Chem 269: 13480–13489). Glutamate receptor RNA editing is differentially regulated (Nutt S L (1994) Neuroreport 5: 1679–1683). Since glutamate receptors are essential for fast excitatory neurotransmission RNA editing may play a critical role in normal brain function and development. Furthermore, dysfunction of RNA editing may have neuropathological consequences and could be related to neurodegenerative diseases (Nutt et al, supra). Evidence suggests that RED1 and DRADA are members of a larger gene family of enzymes that deaminate nuclear transcripts and have distinct but overlapping substrate specificities (Melcher T et al (1996) Nature 379: 460–464).

By rationally directing RNA editing towards the transcripts of base substitution mutations many genetic diseases could be treated. Additionally, directed RNA editing could be used to treat any disease in which specific changes in gene expression would be therapeutic. A new mRNA editing enzyme could satisfy a need in the art by providing a new means for altering mRNA and affecting gene expression. This could allow new treatment options for psoriasis, atherosclerosis, neurological disorders, and any condition in which a specific change in gene expression would be beneficial.

SUMMARY

The present invention discloses a novel human mRNA editing enzyme (hereinafter referred to as REE), characterized as having homology to HEPR (GI 1177798), REPR (GI 585813) and phorbolin I (GI 436941). Accordingly, the invention features a substantially purified mRNA editing enzyme, as shown in amino acid sequence of SEQ ID NO:1, and having characteristics of mRNA editing enzymes.

One aspect of the invention features isolated and substantially purified polynucleotides which encode REE. In a particular aspect, the polynucleotide is the nucleotide sequence of SEQ ID NO:2. In addition, the invention features polynucleotide sequences that hybridize under stringent conditions to SEQ ID NO:2.

The invention further relates to nucleic acid sequence encoding REE, oligonucleotides, peptide nucleic acids (PNA), fragments, portions or antisense molecules thereof. The present invention also relates to an expression vector which includes polynucleotide encoding REE and its use to transform host cells or organisms.

BRIEF DESCRIPTION OF THE FIGURES

FIGS. 1A–1C show the amino acid sequence (SEQ ID NO:1) and nucleic acid sequence (SEQ ID NO:2) of the novel mRNA editing enzyme, REE produced using MacD-NAsis software (Hitachi Software Engineering Co Ltd).

FIG. 2 shows the northern analysis for Incyte Clone 57953 (SEQ ID NO:2) produced electronically using LIFESEQ database (Incyte Pharmaceuticals, Palo Alto Calif.). The percentage abundance is calculated by multiplying the number of transcripts found in the library times 100 and dividing the product by the total number of transcripts in the library.

FIG. 3 shows the amino acid sequence alignments among REE (SEQ ID NO:1), phorbolin I (GI 436941; SEQ ID NO:3), HEPR (GI 1177798; SEQ ID NO:4), and REPR (GI 585813; SEQ ID NO:5) produced using the multisequence alignment program of DNAStar software (DNAStar Inc, Madison Wis.).

DETAILED DESCRIPTION OF THE INVENTION

Definitions

Figure 4:
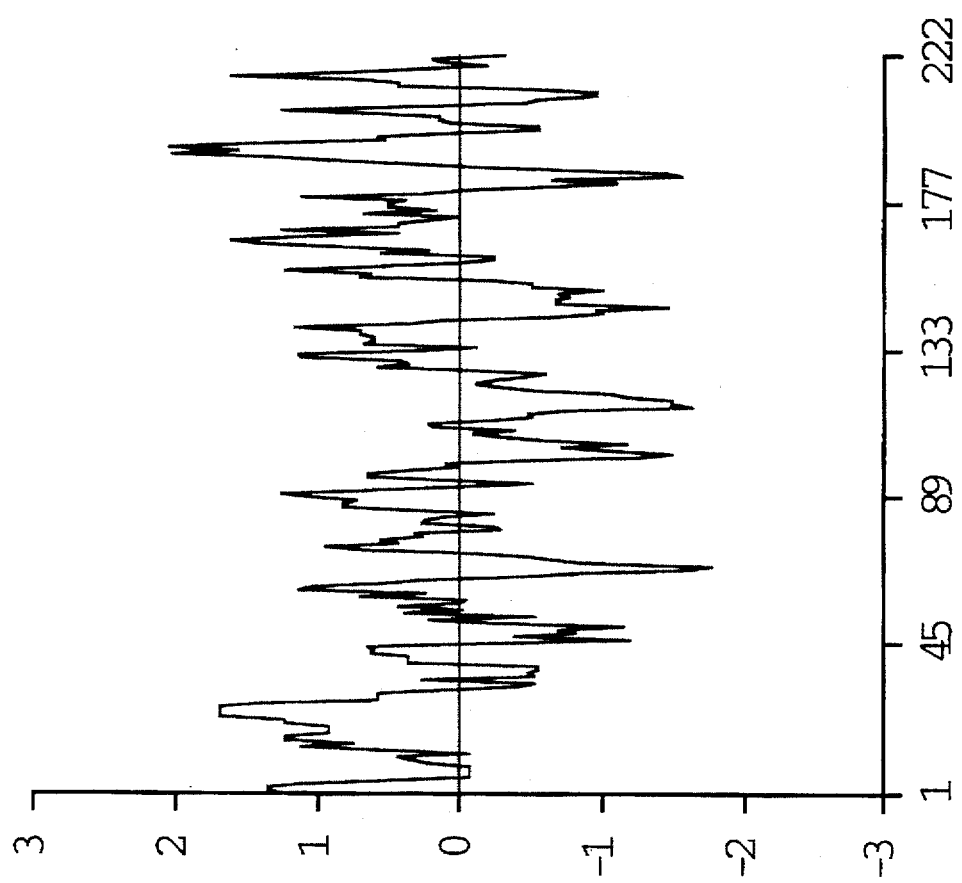
FIG. 4 shows the hydrophobicity plot (generated using MacDNAsis software) for REE, SEQ ID NO:1; the X axis reflects amino acid position, and the negative Y axis, hydrophobicity (FIGS. 4 and 5).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen P E et al (1993) Anticancer Drug Des 8:53–63).

As used herein, REE refers to the amino acid sequence of substantially purified REE obtained from any species, particularly mammalian, including bovine, ovine, porcine, murine, equine, and preferably human, from any source whether natural, synthetic, semi-synthetic or recombinant.

A "variant" of REE is defined as an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a REE having structural, regulatory or biochemical functions of a naturally occurring REE. Likewise, "immunologically active" defines the capability of the natural, recombinant or synthetic REE, or any oligopeptide thereof, to induce a specific immune response in appropriate animals or cells and to bind with specific antibodies.

The term "derivative" as used herein refers to the chemical modification of a nucleic acid encoding REE or the encoded REE. Illustrative of such modifications would be replacement of hydrogen by an alkyl, acyl, or amino group. A nucleic acid derivative would encode a polypeptide which retains essential biological characteristics of natural REE.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring REE.

A "substitution" results from the replacement of one or more nucleotides or amino acids by different nucleotides or amino acids, respectively.

Description

The present invention relates to a novel human mRNA editing enzyme initially identified among the cDNAs from a skeletal muscle cDNA library (MUSCNOT01) and to the use of the nucleic acid and amino acid sequences in the study, diagnosis, prevention and treatment of disease. cDNAs encoding a portion of REE were found in skeletal muscle and prostate tissue-derived cDNA libraries (FIG. 2).

The present invention also encompasses REE variants. A preferred REE variant is one having at least 80% amino acid sequence similarity to the REE amino acid sequence (SEQ ID NO:1), a more preferred REE variant is one having at least 90% amino acid sequence similarity to SEQ ID NO:1 and a most preferred REE variant is one having at least 95% amino acid sequence similarity to SEQ ID NO:1.

Figure 5:
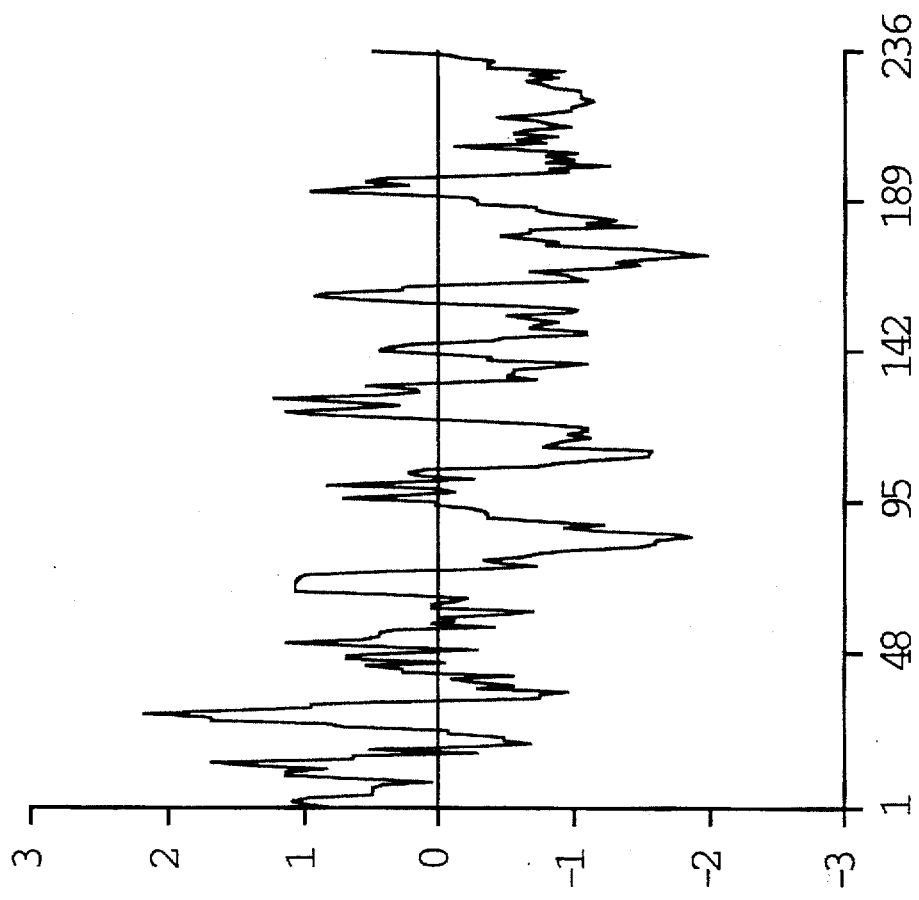
FIG. 5 shows the hydrophobicity plot for HEPR, SEQ ID NO:4.

Nucleic acid encoding the human mRNA editing enzyme of the present invention was first identified in cDNA, Incyte Clone 57953 (SEQ ID NO:2), through a computer-generated search for amino acid sequence alignments. The nucleic acid sequence encoding REE, SEQ ID NO:2; encodes the REE amino acid sequence, SEQ ID NO:1. The present invention is based, in part, on the chemical and structural homology among REE, HEPR (GI 1177798; Hadjiagapiou et al, supra), REPR (GI 585813; Teng B et al (1993) Science 260: 1816–1819), and phorbolin (GI 436941; Madsen PP, unpublished); FIG. 3). REE contains conserved zinc-coordinating residues Cys128 and Cys131, and catalytically active residues Glu100 and Pro127, necessary for both RNA editing and cytidine deaminase activities. REE also contains conserved residue His98, required for RNA binding, RNA editing, and cytidine deaminase activities. REE has 23% identity to HEPR, 24% identity to REPR, and 32% identity to a partial sequence of phorbolin I. As illustrated by FIGS. 4 and 5, REE and HEPR have similar hydrophobicity plots suggesting similar configurations. The novel REE is 222 amino acids long and has two potential glycosylation sites.

The REE Coding Sequences

The nucleic acid and deduced amino acid sequences of REE are shown in FIGS. 1A and 1B. In accordance with the invention, any nucleic acid sequence which encodes the amino acid sequence of REE can be used to generate recombinant molecules which express REE. In a specific embodiment described herein, a nucleotide sequence encoding a portion of REE was first isolated as Incyte Clone 57953 from a skeletal muscle cDNA library (MUSCNOT01).

It will be appreciated by those skilled in the art that as a result of the degeneracy of the genetic code, a multitude of REE-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring REE, and all such variations are to be considered as being specifically disclosed.

Although nucleotide sequences which encode REE and its variants are preferably capable of hybridizing to the nucleotide sequence of the naturally occurring REE under appropriately selected conditions of stringency, it may be advantageous to produce nucleotide sequences encoding REE or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding REE and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a REE and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding REE or any portion thereof.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*,; Vol 152, Academic Press, San Diego Calif.) incorporated herein by reference, and confer may be used at a defined stringency.

Altered nucleic acid sequences encoding REE which may be used in accordance with the invention include deletions, insertions or substitutions of different nucleotides resulting in a polynucleotide that encodes the same or a functionally equivalent REE. The protein may also show deletions, insertions or substitutions of amino acid residues which produce a silent change and result in a functionally equivalent REE. Deliberate amino acid substitutions may be made on the basis of similarity in polarity, charge, solubility, hydrophobicity, hydrophilicity, and/or the amphipathic nature of the residues as long as the biological activity of REE is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of REE. As used herein, an "allele" or "allelic sequence" is an alternative form of REE. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding REE may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use PCR, nested primers and PromoterFinder libraries to walk in genomic DNA (PromoterFinder™ Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–8).

Expression of the Nucleotide Sequence

In accordance with the present invention, polynucleotide sequences which encode REE, fragments of the polypeptide, fusion proteins or functional equivalents thereof may be used in recombinant DNA molecules that direct the expression of REE in appropriate host cells. Due to the inherent degeneracy of the genetic code, other DNA sequences which encode substantially the same or a functionally equivalent amino acid sequence, may be used to clone and express REE. As will be understood by those of skill in the art, it may be advantageous to produce REE-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of REE expression or to produce recombinant RNA transcripts having desirable properties, such as a longer half-life, than transcripts produced from naturally occurring sequence.

The nucleotide sequences of the present invention can be engineered in order to alter a REE coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotides encoding REE may be ligated to a heterologous sequence to encode a fusion protein. For example, for screening of peptide libraries for inhibitors of REE activity, it may be useful to encode a chimeric REE protein that is recognized by a commercially available antibody. A fusion protein may also be engineered to contain a cleavage site located between a REE sequence and the heterologous protein sequence, so that the REE may be cleaved and purified away from the heterologous moiety.

In an alternate embodiment of the invention, the coding sequence of REE may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a REE amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be prepared substantially by high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of REE, or any part thereof, may be altered during direct synthesis and/or combined using chemical methods with sequences from other proteins, or any part thereof, to produce a variant polypeptide.

Expression Systems

In order to express a biologically active REE, the nucleotide sequence encoding REE or its functional equivalent, is inserted into an appropriate expression vector, ie, a vector which contains the necessary elements for the transcription and translation of the inserted coding sequence.

Methods which are well known to those skilled in the art can be used to construct expression vectors containing a REE coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a REE coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of REE, vectors based on SV40 or EBV may be used with an appropriate selectable marker.

In bacterial systems, a number of expression vectors may be selected depending upon the use intended for REE. For example, when large quantities of REE are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the REE coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding REE may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express REE is an insect system. In one such system, *Autographa californica* nuclear polyhedrosis virus (AcNPV) is used as a vector to express foreign genes in *Spodoptera frugiperda* cells or in Trichoplusia larvae. The REE coding sequence may be cloned into a nonessential region of the virus, such as the polyhedrin gene, and placed under control of the polyhedrin promoter. Successful insertion of REE will render the polyhedrin gene inactive and produce recombinant virus lacking coat protein coat. The recombinant viruses are then used to infect *S. frugiperda* cells or Trichoplusia larvae in which REE is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a REE coding sequence may be ligated into an adenovirus transcription/translation complex consisting of the late promoter and tripartite leader sequence. Insertion in a nonessential E1 or E3 region of the viral genome will result in a viable virus capable of expressing REE in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a REE sequence. These signals include the ATG initiation codon and adjacent sequences. In cases where REE, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express REE may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the REE is inserted within a marker gene sequence, recombinant cells containing REE can be identified by the absence of marker gene function. Alternatively, a marker gene can be placed in tandem with a REE sequence under the control of a single promoter. Expression of the marker gene in response to induction or selection usually indicates expression of the tandem REE as well.

Alternatively, host cells which contain the coding sequence for REE and express REE may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding REE can be detected by DNA-DNA or DNA-RNA hybridization or amplification using probes, portions or fragments of polynucleotides encoding REE. Nucleic acid amplification based assays involve the use of oligonucleotides or oligomers based on the REE-encoding sequence to detect transformants containing DNA or RNA encoding REE. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of REE, using either polyclonal or monoclonal antibodies specific for the protein are known in the art. Examples include enzyme-linked immunosorbent assay (ELISA), radioimmunoassay (RIA) and fluorescent activated cell sorting (PACS). A two-site, monoclonal-based immunoassay utilizing monoclonal antibodies reactive to two non-interfering epitopes on REE is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding REE include oligolabeling, nick translation, end-labeling or PCR amplification using a labeled nucleotide. Alternatively, the REE sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of REE

Host cells transformed with a nucleotide sequence encoding REE may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding REE can be designed with signal sequences which direct secretion of REE through a prokaryotic or eukaryotic cell membrane. Other recombinant constructions may join REE to nucleotide sequence encoding a polypeptide domain which will facilitate purification of soluble proteins (Kroll D J et al (1993) DNA Cell Biol 12:441–53; cf discussion of vectors infra containing fusion proteins).

REE may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and REE is useful to facilitate purification. One such expression vector provides for expression of a fusion protein compromising an REE and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying REE from the fusion protein.

In addition to recombinant production, fragments of REE may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of REE may be chemically synthesized separately and combined using chemical methods to produce the full length molecule.

Uses of REE

The rationale for use of the nucleotide and polypeptide sequences disclosed herein is based in part on the chemical and structural homology among the novel human mRNA editing enzyme disclosed herein, HEPR (GI 1177798; Hadjiagapiou et al, supra), REPR (GI 585813; Teng et al, supra), and phorbolin I (GI 436941; Madsen et al, supra).

Accordingly, REE be used to direct RNA editing towards mutated RNA sequences that cause genetic diseases. Additionally, directed RNA editing could be used to treat any disease in which specific changes in gene expression would be therapeutic. REE or a REE derivative may be used to treat atherosclerosis or psoriasis, restore alpha-galactosidase activity in patients with Fabry's disease, or to treat neurodegenerative diseases that are found to be caused by defective glutamate receptor function.

In those conditions where mRNA editing enzyme activity is not desirable, cells could be transfected with antisense sequences of REE-encoding polynucleotides or provided with inhibitors of REE.

REE Antibodies

REE-specific antibodies are useful for the diagnosis of conditions and diseases associated with expression of REE. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

REE for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of REE amino acids may be fused with those of another protein such as keyhole limpet hemocyanin and antibody produced against the chimeric molecule. Procedures well known in the art can be used for the production of antibodies to REE.

For the production of antibodies, various hosts including goats, rabbits, rats, mice, etc may be immunized by injection with REE or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to REE may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce REE-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for REE may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between REE and its specific antibody and the measurement of complex formation. A two-site, monoclonal-based immunoassay utilizing monoclonal antibodies reactive to two noninterfering epitopes on a specific REE protein is preferred, but a competitive binding assay may also be employed. These assays are described in Maddox D E et al (1983, J Exp Med 158:1211).

Diagnostic Assays Using REE Specific Antibodies

Particular REE antibodies are useful for the diagnosis of conditions or diseases characterized by expression of REE or in assays to monitor patients being treated with REE, agonists or inhibitors. Diagnostic assays for REE include methods utilizing the antibody and a label to detect REE in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring REE, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on REE is preferred, but a competitive binding assay may be employed. These assays are described, among other places, in Maddox, DE et al (1983, J Exp Med 158:1211).

In order to provide a basis for diagnosis, normal or standard values for REE expression must be established. This is accomplished by combining body fluids or cell extracts taken from normal subjects, either animal or human, with antibody to REE under conditions suitable for complex formation which are well known in the art. The amount of standard complex formation may be quantified by comparing various artificial membranes containing known quantities of REE with both control and disease samples from biopsied tissues. Then, standard values obtained from normal samples may be compared with values obtained from samples from subjects potentially affected by disease. Deviation between standard and subject values establishes the presence of disease state.

Drug Screening

REE, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between REE and the agent being tested, may be measured.

Another technique for drug screening which may be used provides for high throughput screening of compounds having suitable binding affinity to the REE is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of REE and washed. Bound REE is then detected by methods well known in the art. Purified REE can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding REE specifically compete with a test compound for binding REE. In this manner, the antibodies can be used to detect the presence of any peptide which shares one or more antigenic determinants with REE.

Uses of the Polynucleotide Encoding REE

A polynucleotide encoding REE, or any part thereof, may be used for diagnostic and/or therapeutic purposes. For diagnostic purposes, polynucleotides encoding REE of this invention may be used to detect and quantitate gene expression in biopsied tissues in which expression of REE may be implicated. The diagnostic assay is useful to distinguish between absence, presence, and excess expression of REE and to monitor regulation of REE levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding REE or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding REE, alleles or related sequences.

Probes may also be used for the detection of related sequences and should preferably contain at least 50% of the nucleotides from any of these REE encoding sequences. The hybridization probes of the subject invention may be derived from the nucleotide sequence of SEQ ID NO:2 or from genomic sequence including promoter, enhancer elements and introns of the naturally occurring REE. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding REE include the cloning of nucleic acid sequences encoding REE or REE derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Polynucleotide sequences encoding REE may be used for the diagnosis of conditions or diseases with which the expression of REE is associated. For example, polynucleotide sequences encoding REE may be used in hybridization or PCR assays of fluids or tissues from biopsies to detect REE expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding REE disclosed herein provide the basis for assays that detect activation or induction associated with muscle wasting. The nucleotide sequence encoding REE may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding REE in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for REE expression must be established. This is accomplished by combining body fluids or cell extracts taken from normal subjects, either animal or human, with REE, or a portion thereof, under conditions suitable for hybridization or amplification. Standard hybridization may be quantified by comparing the values obtained for normal subjects with a dilution series of REE run in the same experiment where a known amount of a substantially purified REE is used. Standard values obtained from normal samples may be compared with values obtained from samples from patients afflicted with REE-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the REE sequence. Such oligomers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. For example, the presence of a relatively high amount of REE in extracts of biopsied tissues may indicate the onset of muscle wasting. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding mRNA editing enzymes and its expression profile, polynucleotide sequences encoding REE disclosed herein may be useful in the treatment of conditions such as atherosclerosis or psoriasis.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding REE. See, for example, the techniques described in Sambrook et al (supra) and Ausubel et al (supra).

The polynucleotides comprising full length CDNA sequence and/or its regulatory elements enable researchers to use sequences encoding REE as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding REE can be turned off by transfecting a cell or tissue with expression vectors which express high levels of a desired REE-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding REE, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding REE.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding REE. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for REE disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for REE can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding REE on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example a sequence tagged site based map of the human genome was recently published by the Whitehead-MIT Center for Genomic Research (Hudson T J et al (1995) Science 270:1945–1954). Often the placement of a gene on the chromosome of another mammalian species such as a mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of REE, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that REE or an REE derivative can be delivered in a suitable formulation to edit mRNA of proteins involved in diseases, such as atherosclerosis and psoriasis. Similarly, administration of REE antagonists may also inhibit the activity or shorten the lifespan of this protein and decrease specific mRNA editing activity.

The examples below are provided to illustrate the subject invention and are not included for the purpose of limiting the invention.

EXAMPLES

I DNA Library Construction

The normal skeletal muscle used for this library was obtained from the Keystone Skin Bank, International Institute for the Advancement of Medicine (Exton, Pa.). Five grams of normal skeletal muscle tissue from a 47 year old male was flash frozen, ground in a mortar and pestle, and lyzed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to a paramagnetic particle (Promega Corp, Madison Wis.) and sent to Stratagene (11011 North Torrey Pines Road, La Jolla, Calif. 92037). Stratagene prepared the CDNA library using oligo d(T) priming. Synthetic adapter oligonucleotides were ligated onto the cDNA molecules enabling them to be inserted into the Uni-ZAP- vector system (Stratagene). This allowed high efficiency unidirectional (sense orientation) lambda library construction and the convenience of a plasmid system with blue/white color selection to detect clones with cDNA insertions.

The quality of the cDNA library was screened using DNA probes, and then, the pBluescript phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom constructed library phage particles were infected into E. coli host strain XL1-Blue (Stratagene). The high transformation efficiency of this bacterial strain increases the probability that the CDNA library will contain rare, under-represented clones. Alternative unidirectional vectors might include, but are not limited to, pcDNAI (Invitrogen) and pSHlox-1 (Novagen).

II Isolation of CDNA Clones

The phagemid forms of individual cDNA clones were obtained by the in vivo excision process, in which the host bacterial strain was coinfected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for lactamase, the newly transformed bacteria were selected on medium containing ampicillin.

Phagemid DNA was also purified using the QIAWELL-8 Plasmid Purification System from the QIAGEN DNA Purification System (QIAGEN Inc, Chatsworth, Calif.). This product provides a convenient, rapid and reliable high-throughput method for lysing the bacterial cells and isolating highly purified phagemid DNA using QIAGEN anion-exchange resin particles with EMPORETM membrane technology from 3M in a multiwell format. The DNA was eluted from the purification resin and prepared for DNA sequencing and other analytical manipulations.

III Homology Searching of CDNA Clones and Their Deduced Proteins

Each CDNA was compared to sequences in GenBank using a search algorithm developed by Applied Biosystems and incorporated into the INHERIT 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored-with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of REE-Encoding Polynucleotides to Full Length or to Recover Regulatory Elements Full length REE-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known REE-encoding sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected CDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 40° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Betani (LB)-agar (Sambrook J et al, supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [γ-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing 10$^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The REE-encoding sequence, or any part thereof, is used to inhibit in vivo or in vitro expression of naturally occurring REE. Although use of antisense oligonucleotides, comprising about 20 base-pairs, is specifically described, essentially the same procedure is used with larger cDNA fragments. An oligonucleotide based on the coding sequence of REE, as shown in FIGS. 1A and 1B, is used to inhibit expression of naturally occurring REE. The complementary oligonucleotide is designed from the most unique 5' sequence as shown in FIGS. 1A and 1B and used either to inhibit transcription by preventing promoter binding to the upstream nontranslated sequence or translation of an REE-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A and 1B.

VIII Expression of REE

Expression of the REE is accomplished by subcloning the cDNAs into appropriate vectors and transfecting the vectors into host cells. In this case, the cloning vector, pSport, previously used for the generation of the cDNA library is used to express REE in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length REE-encoding sequence. The signal sequence directs the secretion of REE into the bacterial growth media which can be used directly in the following assay for activity.

IX REE Activity

REE's deaminase activity can be measured by a method described by MacGinntie A J et al (1995, J Biol Chem 270: 14768–14775). Substantially purified REE is incubated with 3.3 uCi of [$^3$H] deoxycytidine and 250 uM cytidine in a total volume of 10 ul in a buffer containing 45 mM TRIS, pH 7.5. After timed incubations the reaction is quenched by the addition of 2 ul of 10 ug/ul each deoxycytidine and deoxyuridine. Any insoluble material is removed by centrifugation for 2 minutes at full speed in a microcentrifuge, and 4 ul of the reaction mixture is applied to a polyethyleneiminecellulose thin layer chromatographic plate. The corresponding deoxycytidine and deoxyuridine bands are visualized by exposure to UV light and scraped into scintillation fluid for quantification by liquid scintillation spectroscopy.

X Production of REE Specific Antibodies

REE substantially purified using PAGE electrophoresis (Sambrook, supra) is used to immunize rabbits and to produce antibodies using standard protocols. The amino acid sequence translated from REE is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring REE Using Specific Antibodies

Naturally occurring or recombinant REE is substantially purified by immunoaffinity chromatography using antibodies specific for REE. An immunoaffinity column is constructed by covalently coupling REE antibody to an activated chromatographic resin such as CnBr-activated Sepharose (Pharmacia Biotech). After the coupling, the resin is blocked and washed according to the manufacturer's instructions.

Media containing REE is passed over the immunoaffinity column, and the column is washed under conditions that allow the preferential absorbance of REE (eg, high ionic strength buffers in the presence of detergent). The column is eluted under conditions that disrupt antibody/REE binding (eg, a buffer of pH 2–3 or a high concentration of a chaotrope such as urea or thiocyanate ion), and REE is collected.

XII Identification of Molecules Which Interact with REE

REE, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled REE, washed and any wells with labeled REE complex are assayed. Data obtained using different concentrations of REE are used to calculate values for the number, affinity, and association of REE with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide sequence encoding a polypeptide comprising the amino acid sequence of SEQ ID NO:1.

2. An isolated and purified polynucleotide sequence of claim 1 consisting of the sequence of SEQ ID NO:2 or degenerate variants thereof.

3. An isolated and purified polynucleotide sequence fully complementary to the sequence of SEQ ID NO:2 or degenerate variants thereof.

4. An isolated and purified polynucleotide sequence of claim 1 consisting of a polynucleotide sequence that hybridizes under stringent hybridization conditions to the sequence of SEQ ID NO:2.

5. A recombinant expression vector containing a polynucleotide sequence of claim 1.

6. A recombinant host cell comprising a polynucleotide sequence of claim 1.

7. A method for producing a polypeptide comprising the amino acid sequence shown in SEQ ID NO:1, the method comprising the steps of:

a) culturing the host cell of claim 6 under conditions suitable for the expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 222 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: MUSCNOT1
        ( B ) CLONE: 57953

( x i ) SEQUENCE DESCRIPTION: SEQ ID NO:1:

```
Met Ala Gln Lys Glu Glu Ala Ala Val Ala Thr Glu Ala Ala Ser Gln
 1               5                  10                  15

Asn Gly Glu Asp Leu Glu Asn Leu Asp Asp Pro Glu Lys Leu Lys Glu
             20                  25                  30

Leu Ile Glu Leu Pro Pro Phe Glu Ile Val Thr Gly Glu Arg Leu Pro
         35                  40                  45

Ala Asn Phe Phe Lys Phe Gln Phe Arg Asn Val Glu Tyr Ser Ser Gly
     50                  55                  60

Arg Asn Lys Thr Phe Leu Cys Tyr Val Val Glu Ala Gln Gly Lys Gly
 65                  70                  75                  80

Gly Gln Val Gln Ala Ser Arg Gly Tyr Leu Glu Asp Glu His Ala Ala
                 85                  90                  95

Ala His Ala Glu Glu Ala Phe Phe Asn Thr Ile Leu Pro Ala Phe Asp
                100                 105                 110

Pro Ala Leu Arg Tyr Asn Val Thr Trp Tyr Val Ser Ser Ser Pro Cys
             115                 120                 125

Ala Ala Cys Ala Asp Arg Ile Xaa Lys Thr Leu Ser Lys Thr Lys Asn
     130                 135                 140

Leu Arg Leu Leu Ile Leu Val Gly Arg Leu Phe Met Trp Glu Glu Pro
145                 150                 155                 160

Glu Ile Gln Ala Ala Leu Lys Lys Leu Lys Glu Ala Gly Cys Lys Leu
                 165                 170                 175

Arg Ile Met Lys Pro Gln Asp Phe Glu Tyr Val Trp Gln Asn Phe Val
             180                 185                 190

Glu Gln Glu Glu Gly Glu Ser Lys Ala Phe Gln Pro Trp Glu Asp Ile
             195                 200                 205

Gln Glu Asn Phe Leu Tyr Tyr Glu Glu Lys Leu Ala Asp Ile
             210                 215                 220
```

( 2 ) INFORMATION FOR SEQ ID NO:2:

( i ) SEQUENCE CHARACTERISTICS:

(A) LENGTH: 891 base pairs
(B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY: MUSCNOT1
(B) CLONE: 57953

(xi) SEQUENCE DESCRIPTION: SEQ ID NO:2:

```
TGNCGCNCTA TATGCTTGGC NTCCTCCGNG AACCTGTCAT CCCGGCNCCA TTTNANNAGC    60
TGACAGCTGC TTGGGACTCT GCCGCCAGGG CCTGGCCCAG ACCTGCCTGC CTCTCTCCTC   120
TCCCTCAGTG ACTCCTGAGC CACAGCCCCT CCATGGCCCA GAAGGAAGAG GCTGCTGTGG   180
CCACTGAGGC TGCCTCCCAG AATGGGGAGG ATCTGGAGAA CCTGGACGAC CCTGAGAAGC   240
TGAAAGAGCT GATTGAGCTG CCGCCCTTTG AGATTGTCAC AGGAGAACGG CTGCCTGCCA   300
ACTTCTTTAA ATTCCAGTTC CGGAATGTGG AGTACAGTTC CGGGAGGAAC AAGACCTTCC   360
TCTGCTATGT GGTTGAAGCA CAGGGCAAGG GGGCCAAGT GCAGGCATCT CGGGGATACC    420
TAGAGGATGA GCATGCGGCT GCCCATGCAG AGGAAGCTTT CTTCAACACC ATCCTGCCAG   480
CCTTCGACCC AGCCCTGCGG TACAATGTCA CCTGGTATGT GTCCTCCAGC CCCTGTGCAG   540
CGTGTGCTGA CCGCATTAYC AAAACCCTTA GCAAGACCAA GAACCTGCGT CTGCTCATTC   600
TGGTGGGTCG ACTCTTCATG TGGGAGGAGC CGGAGATCCA GGCTGCTCTG AAGAAGCTGA   660
AGGAGGCTGG CTGTAAACTG CGCATCATGA AGCCCAGGA CTTCGAATAT GTCTGGCAGA    720
ATTTTGTGGA GCAAGAAGAG GGTGAATCCA AGGCCTTTCA RCCCTGGGAG GACATTCAGG   780
AGAACTTCCT ATACTACGAG GAGAAGTTGG CAGACATCTG AAGTAGGGCA ACTGGGTTTC   840
CTCACGGATT CCTGTCTGCC ACCAAGAGAC AGCAATGCAT GTACAGCCAT T             891
```

(2) INFORMATION FOR SEQ ID NO:3:

(i) SEQUENCE CHARACTERISTICS:
(A) LENGTH: 116 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 436941

(xi) SEQUENCE DESCRIPTION: SEQ ID NO:3:

```
Asn Ser Ala Arg Glu Ile Tyr Arg Val Thr Trp Phe Ile Ser Trp Ser
 1               5                  10                  15

Pro Cys Phe Ser Trp Gly Cys Ala Gly Glu Val Arg Ala Phe Leu Gln
            20                  25                  30

Glu Asn Thr His Val Arg Leu Pro Ile Phe Ala Ala Arg Ile Tyr Asp
        35                  40                  45

Tyr Asp Pro Leu Tyr Lys Glu Ala Leu Gln Met Leu Arg Asp Ala Gly
    50                  55                  60

Ala Gln Val Ser Ile Met Thr Tyr Asp Glu Phe Glu Tyr Cys Trp Asp
65                  70                  75                  80

Thr Phe Val Tyr Arg Gln Gly Cys Pro Phe Gln Pro Trp Asp Gly Leu
                85                  90                  95

Glu Glu His Ser Gln Ala Leu Ser Gly Arg Leu Arg Ala Ile Leu Gln
                100                 105                 110
```

Asn Gln Gly Asn
            115

(2) INFORMATION FOR SEQ ID NO:4:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1177798

(xi) SEQUENCE DESCRIPTION: SEQ ID NO:4:

Met Thr Ser Glu Lys Gly Pro Ser Thr Gly Asp Pro Thr Leu Arg Arg
 1           5                  10                 15

Arg Ile Glu Pro Trp Glu Phe Asp Val Phe Tyr Asp Pro Arg Glu Leu
            20                 25                 30

Arg Lys Glu Ala Cys Leu Leu Tyr Glu Ile Lys Trp Gly Met Ser Arg
        35                 40                 45

Lys Ile Trp Arg Ser Ser Gly Lys Asn Thr Thr Asn His Val Glu Val
    50                 55                 60

Asn Phe Ile Lys Lys Phe Thr Ser Glu Arg Asp Phe His Pro Ser Ile
65                 70                 75                  80

Ser Cys Ser Ile Thr Trp Phe Leu Ser Trp Ser Pro Cys Trp Glu Cys
                85                 90                 95

Ser Gln Ala Ile Arg Glu Phe Leu Ser Arg His Pro Gly Val Thr Leu
            100                105                110

Val Ile Tyr Val Ala Arg Leu Phe Trp His Met Asp Gln Gln Asn Arg
        115                120                125

Gln Gly Leu Arg Asp Leu Val Asn Ser Gly Val Thr Ile Gln Ile Met
    130                135                140

Arg Ala Ser Glu Tyr Tyr His Cys Trp Arg Asn Phe Val Asn Tyr Pro
145                150                155                160

Pro Gly Asp Glu Ala His Trp Pro Gln Tyr Pro Pro Leu Trp Met Met
                165                170                175

Leu Tyr Ala Leu Glu Leu His Cys Ile Ile Leu Ser Leu Pro Pro Cys
            180                185                190

Leu Lys Ile Ser Arg Arg Trp Gln Asn His Leu Thr Phe Phe Arg Leu
        195                200                205

His Leu Gln Asn Cys His Tyr Gln Thr Ile Pro Pro His Ile Leu Leu
    210                215                220

Ala Thr Gly Leu Ile His Pro Ser Val Ala Trp Arg
225                230                235

(2) INFORMATION FOR SEQ ID NO:5:

(i) SEQUENCE CHARACTERISTICS:
        (A) LENGTH: 229 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 585813

(xi) SEQUENCE DESCRIPTION: SEQ ID NO:5:

```
Met Ser Ser Glu Thr Gly Pro Val Ala Val Asp Pro Thr Leu Arg Arg
 1           5                  10                  15
Arg Ile Glu Pro His Glu Phe Glu Val Phe Phe Asp Pro Arg Glu Leu
             20                  25                  30
Arg Lys Glu Thr Cys Leu Leu Tyr Glu Ile Asn Trp Gly Gly Arg His
         35                  40                  45
Ser Ile Trp Arg His Thr Ser Gln Asn Thr Asn Lys His Val Glu Val
     50                  55                  60
Asn Phe Ile Glu Lys Phe Thr Thr Glu Arg Tyr Phe Cys Pro Asn Thr
 65                  70                  75                  80
Arg Cys Ser Ile Thr Trp Phe Leu Ser Trp Ser Pro Cys Gly Glu Cys
                 85                  90                  95
Ser Arg Ala Ile Thr Glu Phe Leu Ser Arg Tyr Pro His Val Thr Leu
             100                 105                 110
Phe Ile Tyr Ile Ala Arg Leu Tyr His His Ala Asp Pro Arg Asn Arg
         115                 120                 125
Gln Gly Leu Arg Asp Leu Ile Ser Ser Gly Val Thr Ile Gln Ile Met
     130                 135                 140
Thr Glu Gln Glu Ser Gly Tyr Cys Trp Arg Asn Phe Val Asn Tyr Ser
145                 150                 155                 160
Pro Ser Asn Glu Ala His Trp Pro Arg Tyr Pro His Leu Trp Val Arg
                 165                 170                 175
Leu Tyr Val Leu Glu Leu Tyr Cys Ile Ile Leu Gly Leu Pro Pro Cys
             180                 185                 190
Leu Asn Ile Leu Arg Arg Lys Gln Pro Gln Leu Thr Phe Phe Thr Ile
         195                 200                 205
Ala Leu Gln Ser Cys His Tyr Gln Arg Leu Pro Pro His Ile Leu Trp
     210                 215                 220
Ala Thr Gly Leu Lys
225
```